United States Patent
Pawlak et al.

(10) Patent No.: US 9,180,426 B2
(45) Date of Patent: Nov. 10, 2015

(54) SCRUBBER FOR METHANOL PRODUCTION SYSTEM

(75) Inventors: Nathan A Pawlak, Marquette, MI (US); Robert W Carr, Bloomington, MN (US)

(73) Assignee: Gas Technologies, LLC, Walloon Lake, MI (US)

( * ) Notice: Subject to any disclaimer, the term of this patent is extended or adjusted under 35 U.S.C. 154(b) by 1005 days.

(21) Appl. No.: 11/446,371

(22) Filed: Jun. 2, 2006

(65) Prior Publication Data

US 2006/0223892 A1 Oct. 5, 2006

Related U.S. Application Data

(63) Continuation-in-part of application No. 11/319,093, filed on Dec. 27, 2005, and a continuation-in-part of application No. 10/901,717, filed on Jul. 29, 2004, now Pat. No. 7,179,843.

(51) Int. Cl.

| | | |
|---|---|---|
| *C07C 27/14* | (2006.01) | |
| *B01J 19/24* | (2006.01) | |
| *B01D 3/14* | (2006.01) | |
| *B01D 53/14* | (2006.01) | |
| *B01D 53/18* | (2006.01) | |
| *B01J 4/00* | (2006.01) | |
| *B01J 19/00* | (2006.01) | |
| *B01J 19/26* | (2006.01) | |
| *C07C 29/50* | (2006.01) | |

(52) U.S. Cl.
CPC .............. *B01J 19/2415* (2013.01); *B01D 3/14* (2013.01); *B01D 53/1487* (2013.01); *B01D 53/18* (2013.01); *B01J 4/002* (2013.01); *B01J 19/006* (2013.01); *B01J 19/26* (2013.01); *C07C 29/50* (2013.01); *B01D 2257/504* (2013.01); *B01D 2257/704* (2013.01); *B01J 2219/00006* (2013.01); *B01J 2219/00123* (2013.01); *B01J 2219/00159* (2013.01); *B01J 2219/00777* (2013.01); *B01J 2219/182* (2013.01); *B01J 2219/1943* (2013.01)

(58) Field of Classification Search
CPC ....................................................... C07C 27/14
USPC .......................................... 422/187; 518/725
See application file for complete search history.

(56) References Cited

U.S. PATENT DOCUMENTS

| | | | |
|---|---|---|---|
| 1,038,547 A | 9/1912 | Fernekes | |
| 1,500,080 A | 7/1924 | Kloppenburg | |
| 1,776,771 A | 9/1930 | Boomer | |
| 2,007,116 A * | 7/1935 | Walker | 568/469.9 |
| 2,128,909 A * | 9/1938 | Bludworth | 568/950 |
| 2,196,188 A | 4/1940 | Bone et al. | |
| 2,244,241 A | 6/1941 | Bryce | |
| 2,384,028 A | 9/1945 | Hall | |
| 2,467,993 A | 4/1949 | Rossman | |
| 2,722,553 A * | 11/1955 | Mullen, II | 568/482 |
| 2,922,809 A | 1/1960 | Oberdorfer, Jr. | |
| 3,027,411 A | 3/1962 | Murphy | |
| 3,064,029 A * | 11/1962 | White | 518/725 |
| 3,130,026 A | 4/1964 | Becker | |
| 3,145,220 A | 8/1964 | Bartok | |
| 3,232,991 A | 2/1966 | Magee | |
| 3,483,229 A | 12/1969 | Bernard | |
| 3,689,575 A | 9/1972 | Tarhan | |
| 3,718,006 A | 2/1973 | Ranke | |
| 3,920,717 A | 11/1975 | Marion | |
| 3,940,428 A | 2/1976 | Connell et al. | |
| 3,975,172 A | 8/1976 | Ranke | |
| 3,977,203 A | 8/1976 | Hinton et al. | |
| 3,993,457 A | 11/1976 | Cahn et al. | |
| 4,067,972 A | 1/1978 | Oswald et al. | |
| 4,144,314 A | 3/1979 | Doerges et al. | |
| 4,149,940 A | 4/1979 | Pinto | |
| 4,152,407 A | 5/1979 | Fuchs | |
| 4,203,915 A | 5/1980 | Supp et al. | |
| 4,243,457 A | 1/1981 | Mayumi et al. | |
| 4,243,613 A | 1/1981 | Brockhaus et al. | |
| 4,252,548 A | 2/1981 | Markbreiter et al. | |
| 4,271,086 A | 6/1981 | Supp et al. | |
| 4,289,709 A | 9/1981 | Kaiser | |
| 4,289,710 A | 9/1981 | Kaiser | |
| 4,311,671 A | 1/1982 | Notman | |

(Continued)

FOREIGN PATENT DOCUMENTS

| | | |
|---|---|---|
| EP | 0 790 226 | 12/1996 |
| JP | 63001438 | 1/1988 |

(Continued)

OTHER PUBLICATIONS

"Aspect Advanced Sustainable Processes by Engaging Catalytic Technologies—Call for Pre-proposals & Program Outline", Sep. 16, 2003, pp. 1-14.

G. Foulds, et al., "Kinetics, Catalysis, and Reaction Engineering — Homogeneous Gas-Phase Oxidation of Methane Using Oxygen as Oxidant in an Annular Reactor", Ind. Eng. Chem. Res. 1993, 32, pp. 780-787.

D.N. Koert, et al., A flow reactor for the study of homogeneous gas-phase oxidation of hydrocarbons at pressure up to 20 atm (2 MPa), Mar.,1992, 7 pgs.

(Continued)

*Primary Examiner* — Randy Boyer (74) *Attorney, Agent, or Firm* — Brooks Kushman P.C.

(57) ABSTRACT

An apparatus and method of producing methanol is provided that reacts a methane-containing gas and an oxygen-containing gas in a reactor to provide a product stream comprising methanol and formaldehyde. The product stream is scrubbed using a process component absorbent. After scrubbing the product stream, unprocessed methane gas is mixed with the methane-containing gas for reprocessing through the reactor while methanol and formaldehyde is sent to a rectification process for removal.

13 Claims, 3 Drawing Sheets

(56) References Cited

U.S. PATENT DOCUMENTS

| | | |
|---|---|---|
| 4,312,955 A | 1/1982 | Bartley |
| 4,324,567 A | 4/1982 | Ranke et al. |
| 4,346,179 A | 8/1982 | Sugier et al. |
| 4,353,712 A | 10/1982 | Marion et al. |
| 4,366,260 A | 12/1982 | Wainwright et al. |
| 4,374,288 A | 2/1983 | Scragg |
| 4,386,941 A | 6/1983 | Crouch et al. |
| 4,392,869 A | 7/1983 | Marion et al. |
| 4,394,137 A | 7/1983 | Marion et al. |
| 4,400,180 A | 8/1983 | Marion et al. |
| 4,430,316 A | 2/1984 | Ranke et al. |
| 4,443,560 A | 4/1984 | Le Blanc, Jr. et al. |
| 4,476,250 A | 10/1984 | Joyner et al. |
| 4,479,810 A | 10/1984 | Marion et al. |
| 4,490,156 A | 12/1984 | Marion et al. |
| 4,530,826 A | 7/1985 | Ohashi et al. |
| 4,540,712 A | 9/1985 | Dombek |
| 4,564,643 A | 1/1986 | Shibata et al. |
| 4,575,387 A | 3/1986 | Larue et al. |
| 4,606,741 A | 8/1986 | Moreau et al. |
| 4,608,447 A | 8/1986 | Mazanec et al. |
| 4,609,388 A | 9/1986 | Adler et al. |
| 4,614,749 A | 9/1986 | Sapienza et al. |
| 4,618,732 A | 10/1986 | Gesser et al. |
| 4,619,946 A | 10/1986 | Sapienza et al. |
| 4,623,668 A | 11/1986 | Broecker et al. |
| 4,628,065 A | 12/1986 | Prouteau et al. |
| 4,628,066 A | 12/1986 | Bonnell et al. |
| 4,670,473 A | 6/1987 | Walker et al. |
| 4,721,458 A | 1/1988 | Conrad |
| 4,747,858 A | 5/1988 | Gottier |
| 4,760,210 A | 7/1988 | Sweeney |
| 4,782,096 A | 11/1988 | Banquy |
| 4,816,121 A | 3/1989 | Keefer |
| 4,822,393 A | 4/1989 | Markbreiter et al. |
| 4,861,360 A | 8/1989 | Apffel |
| 4,868,221 A | 9/1989 | Sie et al. |
| 4,873,267 A | 10/1989 | Sie et al. |
| 4,888,361 A | 12/1989 | Sie et al. |
| 4,982,023 A | 1/1991 | Han et al. |
| 5,012,029 A | 4/1991 | Han et al. |
| 5,015,798 A | 5/1991 | Han et al. |
| 5,063,250 A | 11/1991 | Murayama et al. |
| 5,067,972 A | 11/1991 | Hemmings et al. |
| 5,132,472 A | 7/1992 | Durante et al. |
| 5,177,279 A | 1/1993 | Harandi |
| 5,180,570 A | 1/1993 | Lee et al. |
| 5,220,080 A | 6/1993 | Lyons et al. |
| 5,384,335 A | 1/1995 | Tierney et al. |
| 5,496,859 A | 3/1996 | Fong et al. |
| 5,631,302 A | 5/1997 | Konig et al. |
| 5,735,936 A | 4/1998 | Minkkinen et al. |
| 5,770,630 A | 6/1998 | Kowal et al. |
| 5,861,441 A | 1/1999 | Waycuilis |
| 5,883,138 A | 3/1999 | Hershkowitz et al. |
| 5,886,056 A | 3/1999 | Hershkowitz et al. |
| 5,959,168 A | 9/1999 | Aalst |
| 6,028,119 A | 2/2000 | Kokubu et al. |
| 6,102,987 A | 8/2000 | Gross et al. |
| 6,139,605 A | 10/2000 | Carnell et al. |
| 6,153,149 A | 11/2000 | Rabitz et al. |
| 6,159,432 A | 12/2000 | Mallinson et al. |
| 6,267,912 B1 | 7/2001 | Hershkowitz et al. |
| 6,300,380 B1 | 10/2001 | Kobayashi et al. |
| 6,328,854 B1 | 12/2001 | Sherman et al. |
| 6,342,091 B1 | 1/2002 | Menzel et al. |
| 6,447,475 B1 | 9/2002 | Castellano |
| 6,595,291 B1 | 7/2003 | Lia et al. |
| 6,625,988 B2 | 9/2003 | Weisenstein et al. |
| 6,632,971 B2 | 10/2003 | Brown et al. |
| 6,645,272 B2 | 11/2003 | Lemaire et al. |
| 6,667,347 B2 | 12/2003 | O'Rear et al. |
| 6,720,359 B2 | 4/2004 | O'Rear et al. |
| 6,726,850 B1 | 4/2004 | Reyes et al. |
| 6,736,955 B2 | 5/2004 | Shaw |
| 6,881,389 B2 | 4/2005 | Paulsen et al. |
| 6,881,758 B2 | 4/2005 | Guillard et al. |
| 6,942,719 B2 | 9/2005 | Stewart |
| 7,028,478 B2 | 4/2006 | Prentice, III |
| 7,067,558 B2 | 6/2006 | Grobys et al. |
| 7,071,238 B2 | 7/2006 | Gamlin et al. |
| 7,083,662 B2 | 8/2006 | Xu et al. |
| 7,108,838 B2 | 9/2006 | McGee |
| 2001/0006615 A1 | 7/2001 | Badano |
| 2002/0177741 A1 | 11/2002 | Allison et al. |
| 2003/0032844 A1 | 2/2003 | Seiki et al. |
| 2003/0065042 A1 | 4/2003 | Shaw |
| 2004/0065199 A1 | 4/2004 | Rojey et al. |
| 2004/0123523 A1 | 7/2004 | Rong et al. |
| 2004/0171701 A1 | 9/2004 | Shaw |
| 2006/0035986 A1 | 2/2006 | Bichkov et al. |
| 2006/0235088 A1 | 10/2006 | Olah et al. |
| 2006/0264683 A1 | 11/2006 | Knox et al. |

FOREIGN PATENT DOCUMENTS

| | | |
|---|---|---|
| JP | 2004 315413 | 11/2004 |
| RU | 2 203 261 | 3/2002 |
| WO | WO 03/031380 | 4/2003 |

OTHER PUBLICATIONS

E. Ranzi, et al., "A New Comprehensive Reaction Mechanism for Combustion of Hydrocarbon Fuels", Prepared for the Twenty-Fifth International Symposium on Combustion Jul. 31- Aug 5, 1994, Dec. 3, 1993, 23 pgs.

V. Arutyunov, "Recent Results on Fast Flow Gas-Phase Partial Oxidation of Lower Alkanes", Journal of Natural Gas Chemistry 13 (2004), 13 pgs.

E.V. Sheverdenkin, et al., "Kinetics of Partial Oxidation of Alkanes at High Ptessures: Oxidation of Ethane and Methane-Ethane Mixtures", Theoretical Foundations of Chemical Engineering, vol. 38, No. 3, 2004, pp. 311-315.

Zang, et al., "Recent Progress in Direct Partial Oxidation of Methane to Methanol", Journal of Natural Gas Chemistry. vol. 12, No. 2, 2003, pp. 81-89.

Burch, et al. "Direct Conversion of Methane into Methanol", J. Chem. Soc., Faraday Trans. 1, 1989, 85(10), pp. 3561-3568.

Lodeng, et al., "Experimental and Modeling Study of the Selective Homogeneous Gas Phase Oxidation of Methane to Methanol", Industrial Engineerng Chemical Res., 1995, pp. 1044-1059.

Henni, et al., "Solubility of Carbon Dioxide in Methyldiethanolamine + Methanol + Water", Journal of Chemical Engineering Data, 1995, 40, pp. 493-495.

R. Bhatnagar, et al., "Methane Conversion in AC Electric Discharges at Ambient Conditions", Plenum Publishing, NY, 1995, pp. 249-264.

C. Liu, et al., "Oxidative Coupling of Methane with AC and DC Corona Discharges", Industrial & Engineering Chemistry Research, vol. 35, No. 10, 1996, pp. 3295-3301.

A. Marafee, et al., "An Experimental Study on the Oxidative Coupling of Methane in a Direct Current Corona Discharge Reactor over $Sr/La_2O_3$ Catalyst", Industrial & Engineering Chemistry Research, vol. 36, No. 3, 1997, pp. 632-637.

C. Liu, et al., "Methane Conversion to Higher Hydrocarbons in a Corona Discharge Over Metal Oxide Catalysts with Oh Groups", 1997, Applied Catalysis A: General 164, pp. 21-33.

D.W. Larkin, et al., "Oxygen Pathways and Carbon Dioxide Utilization in Methane Partial Oxidation in Ambient Temperature Electric Discharges", Energy & Fuels 1998, 12, pp. 740-744.

C. Liu, et al., "Nonoxidative Methane Conversion to Acetylene over Zeolite in a Low Temperature Plasma", Journal of Catalysis 179, 1998, pp. 326-334.

K. Thanyachotpaiboon, et al., "Conversion of Methane to Higher Hydrocarbons in AC Nonequilibrium Plasmas", AIChE Journal, Oct. 1998, vol. 4, No. 10, pp. 2252-2257.

C. Liu, et al., "Experimental Investigations on the Interaction Between Plasmas and Catalyst for Plasma Catalytic Methane Conversion (PCMC) over Zeolites", Natural Gas Conversion V, Studies in Surface Science and Catalysis, vol. 119, 1998, pp. 361-366.

C. Liu, et al., "Comparative Investigations on Plasma Catalytic Methane Conversion to Higher Hydrocarbons over Zeolites", Applied Catalysis A: General 178, 1999, pp. 17-27.

(56) References Cited

OTHER PUBLICATIONS

D.W. Larkin, et al., "Carbon Pathways, $CO_2$ Utilization, and in Situ Product Removal in Low Temperature Plasma Methane Conversion to Methanol", Greenhouse Gas Control Technologies, 1999, pp. 397-402.

C. Liu, et al., "Modification of $N_aY$ Zeolite in a Corona Discharge and its Application for the Reduction of Carbon Dioxide", Greenhouse Gas Control Technologies, 1999, pp. 1103-1105.

C.L. Gordon, et al., "The Production of Hydrogen From Methane Using Tubular Plasma Reactors", Advances in Hydrogen Energy, 2000, pp. 57-67.

D.W. Larkin, et al., "Production of Organic Oxygenates in the Partial Oxidation of Methane in a Silent Electric Discharge Reactor", Ind. Eng. Chem. Res. 2001, 40, pp. 1594-1601.

D.W. Larkin, et al., "Product Selectivity Control and Organic Oxygenate Pathways From Partial Oxidation of Methane in a Silent Electric Discharge Reactor", Ind. Eng. Chem. Res. 2001, 40, pp. 5496-5506.

T.A. Caldwell, et al., "Partial Oxidation of Methane to Form Synthesis Gas in a Tubular AC Plasma Reactor", Studies in Surface Science and Catalysis, vol. 36: Natural Gas Conversion VI, 2001, pp. 265-270.

K. Supat, et al., "Synthesis Gas Production From Partial Oxidation of Methane with Air in AC Electric Gas Discharge", Energy & Fuels, 2003, 17, pp. 474-481.

K. Supat, et al., "Combined Steam Reforming and Partial Oxidation of Methane to Synthesis Gas Under Electrical Discharge", Ind. Engr. Chem. Res., 2003, 42, p. Est: 7.2 (A-H).

* cited by examiner

SCRUBBER FOR METHANOL PRODUCTION SYSTEM

CROSS-REFERENCE TO RELATED APPLICATIONS

This application is a continuation-in-part application of U.S. application Ser. No. 11/319,093 filed on Dec. 27, 2005, now U.S. Pat. No. 8,202,916 issued Jun. 19, 2012, and is a continuation-in-part application of U.S. application Ser. No. 10/901,717 filed on Jul. 29, 2004, now U.S. Pat. No. 7,179,843 issued Feb. 20, 2007. The disclosures of the above applications are incorporated by reference.

FIELD

The present disclosure relates to a system and method for producing methanol.

BACKGROUND

The statements in this section merely provide background information related to the present disclosure and may not constitute prior art.

Methods and apparatuses for the conversion of methane into methanol are known. It is known to carry out a vapor-phase conversion of methane into a synthesis gas (mixture of CO and $H_2$) with its subsequent catalytic conversion into methanol as disclosed, for example, in Karavaev M. M., Leonov B. E., et al "Technology of Synthetic Methanol", Moscow, "Chemistry" 1984, pages 72-125. However, in order to realize this process it is necessary to provide a complicated equipment, to satisfy high requirements to purity of gas, to spend high quantities of energy for obtaining the synthesis gas and for its purification, and to have a significant number of intermittent stages from the process. Also, for medium and small enterprises with the capacity less than 2,000 tons/day it is not efficient.

Russian Patent No. 2,162,460 includes a source of hydrocarbon-containing gas, a compressor and a heater for compression and heating of gas, a source of oxygen-containing gas with a compressor. It further includes successively arranged reactors with alternating mixing and reaction zones and means to supply the hydrocarbon-containing gas into a first mixing zone of the reactor and the oxygen-containing zone into each mixing zone, a recuperative heat exchanger for cooling of the reaction, mixture through a wall by a stream of cold hydrocarbon-containing gas of the heated hydrocarbon-containing gas into a heater, a cooler-condenser, a partial condenser for separation of waste gasses and liquid products with a subsequent separation of methanol, a pipeline for supply of the waste gas into the initial hydrocarbon-containing gas, and a pipeline for supply of waste oxygen-containing products into the first mixing zone of the reactor.

In this apparatus, however, it is not possible to provide a fast withdrawal of heat of the highly exothermic reaction of oxidation of the hydrocarbon-containing gas because of the inherent limitations of the heat exchanger. This leads to the necessity to reduce the quantity of supplied hydrocarbon-containing gas and, further, it reduces the degree of conversion of the hydrocarbon-containing gas. Moreover, even with the use of oxygen as an oxidizer, it is not possible to provide an efficient recirculation of the hydrocarbon-containing gas due to fast increase of concentration of carbon oxides in it. A significant part of the supplied oxygen is wasted for oxidation of CO into $CO_2$, which additionally reduces the degree of conversion of the initial hydrocarbon-containing gas and provides a further overheating of the reaction mixture. The apparatus also requires burning of an additional quantity of the initial hydrocarbon-containing gas in order to provide a stage of rectification of liquid products with vapor. Since it is necessary to cool the gas-liquid mixture after each reactor for separation of liquid products and subsequent heating before a next reactor, the apparatus is substantially complicated, the number of units is increased, and additional energy is wasted.

A further method and apparatus for producing methanol is disclosed in the patent document RU 2,200,731, in which compressed heated hydrocarbon-containing gas and compressed oxygen-containing gas are introduced into mixing zones of successively arranged reactors, and the reaction is performed with a controlled heat pick-up by cooling of the reaction mixture with water condensate so that steam is obtained, and a degree of cooling of the reaction mixture is regulated by parameters of escaping steam, which is used in liquid product rectification stage.

Other patent documents such as U.S. Pat. Nos. 2,196,188; 2,722,553; 4,152,407; 4,243,613; 4,530,826; 5,177,279; 5.959,168 and International Publication WO 96/06901 disclose further solutions for transformation of hydrocarbons.

It is believed that the existing methods and apparatus for producing methanol can be further improved.

SUMMARY

It is accordingly an object of the present disclosure to provide a system and method for producing methanol, which is a further improvement of the existing methods and apparatuses.

It is another feature of the present teachings to provide a system and method for producing methanol which can be used with minimal processing of gas and gas-condensate deposits, and also at any gas consumer, such as power plants, gas distributing and gas reducing stations, chemical production facilities, etc., or small methane producers, (i.e., coal mines, oil production (flares), landfills, farms.)

In keeping with these objects and with others which will become apparent hereinafter, one feature of the present disclosure resides, briefly stated, in a method of producing methanol, which includes the steps of supplying into a reactor a methane-containing gas stream and an oxygen containing gas; oxidizing the methane-containing gas in the reactor using oxygen of the oxygen-containing gas; and, after scrubbing impurities and products of the reaction, including but not limited to carbon dioxide, water, formaldehyde, and methanol, recycling unreacted methane gas into the methane-containing gas stream for further reaction.

Another feature of the present teachings is a system for producing methanol, which has a reactor for receiving and reacting a methane-containing gas stream with an oxygen-containing gas. The system also has a mechanism for supplying into the reactor a non-oxidizing coolant to be directly mixed with a mixture of the methane-containing gas and oxygen containing gas at a later stage of the reaction to inhibit the decomposition of formaldehyde. The coolant functions to inhibit the oxidation or decomposition of the formaldehyde product. Unreacted methane gas is then processed in a scrubber to remove reaction products and contaminants before being recycled back into the methane-containing gas stream. In various embodiments, the scrubber uses a process component absorbent, for example a mixture of methanol and water, and additionally serves as a condenser. The spent absorbent is regenerated after each pass through the scrubber. A side stream may be provided for removal of carbon dioxide, water, formaldehyde, and methanol in an amount substantially equal to that entering the scrubber at steady state.

As can be seen, in accordance with the present teachings, a gas phase oxidation of the methane-containing gas is performed at elevated temperature and pressure in the reaction zone. The reaction mixture is cooled and directed to a scrubber for removal of carbon dioxide, water, methanol, and formaldehyde, and is recycled and combined with the raw methane-containing gas stream. In certain embodiments, cold methane-containing gas is supplied into a regulation zone of the reactor to reduce the reaction temperature, for example by about 30 to about 90° C., and thereby to provide a production and a redistribution of the ratio of products to produce corresponding quantities of methanol and formaldehyde.

The novel features which are considered as characteristic for the present disclosure are set forth in particular in the appended claims. The disclosure itself, however, both as to its construction and its method of operation, together with additional objects and advantages thereof, will be best understood from the following description of specific embodiments when read in connection with the accompanying drawings.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The present disclosure relates to a system and method for reforming hydrocarbon-containing gases, such as alkanes. Alkanes (typically methane and ethane) can be reformed via a homogenous, partial oxidation reaction with oxygen to form oxygenates, for example, methanol and formaldehyde. The partial oxidation reaction of a methane-containing gas may be used to produce primarily methanol, primarily formaldehyde, or virtually any combination of the two products. In order to obtain a desirably high selectivity of oxygenates and avoid deeper oxidation states of the incoming alkanes, the reaction is typically kept very lean of oxygen, for example, between about 1 to about 3%, resulting in a low per-pass conversion. Even then, co-production of deeper oxidized side products such as water and carbon dioxide remain substantial.

The present disclosure includes a method for recovering oxygenates while simultaneously condensing water and methanol from the product gas of a reformation process. An absorption column, also referred to herein as a scrubber, utilizes process components (e.g., methanol and water) as an absorbent to remove formaldehyde and carbon dioxide. The reactor product stream enters the scrubber in the gas phase and a portion of the stream is condensed by and then entrained into the cool absorbent entering the column. As is known in the art, the temperature, pressure, and solvent throughput can be adjusted to enhance recovery as needed to purify the alkane raw material after which it can be sent onto further processing. For most cases, the temperature will be about 0° C. or lower, enhancing the absorption process. This is especially important due to the desirability of recycling the unreacted alkanes and thus boosting overall yield of the otherwise low conversion technology. In various embodiments, the pressure will typically be between 4 and 10 MPa.

Figure 1:
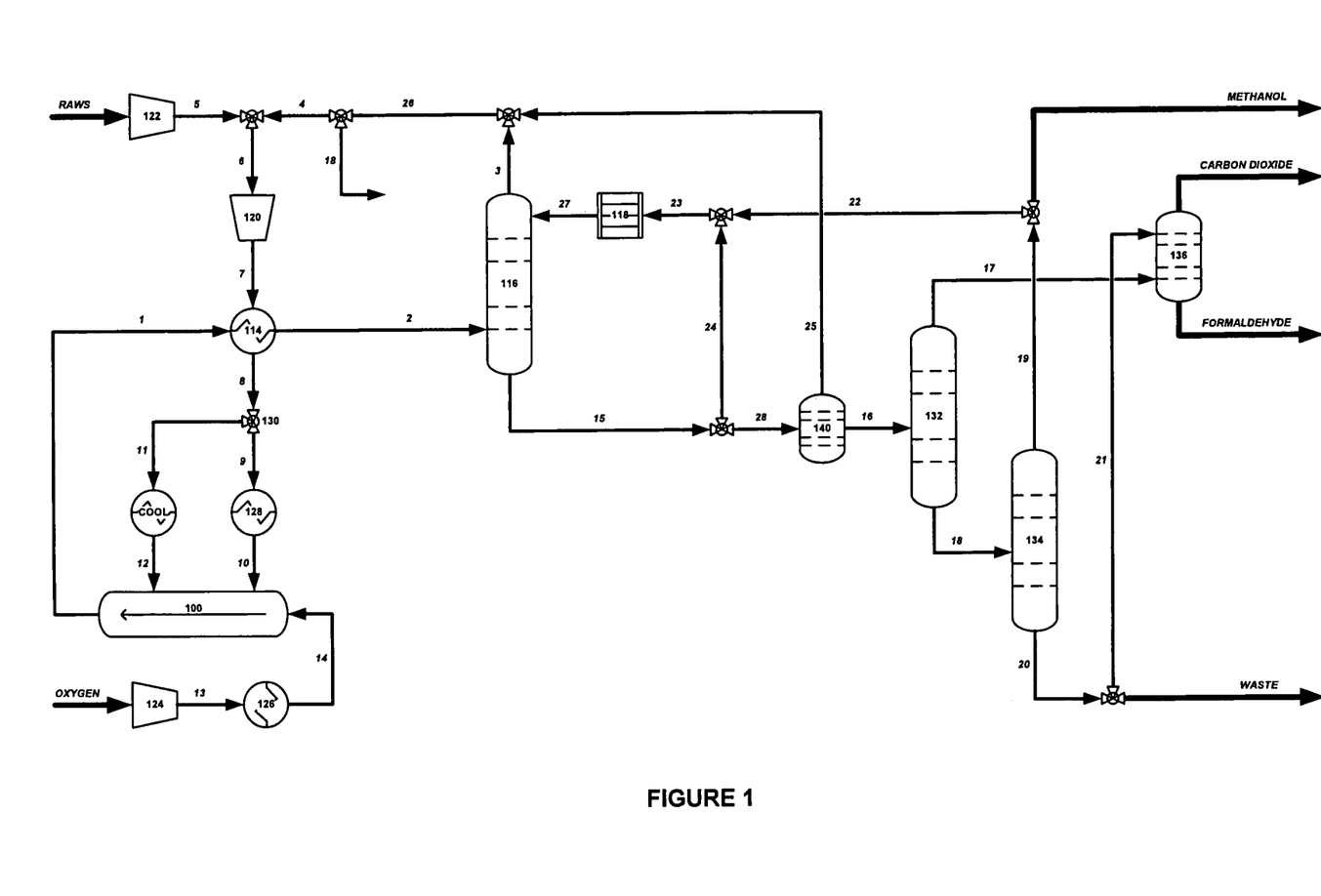
FIG. 1 schematically illustrates a system for producing methanol in accordance with the present teachings.
Figure 2:
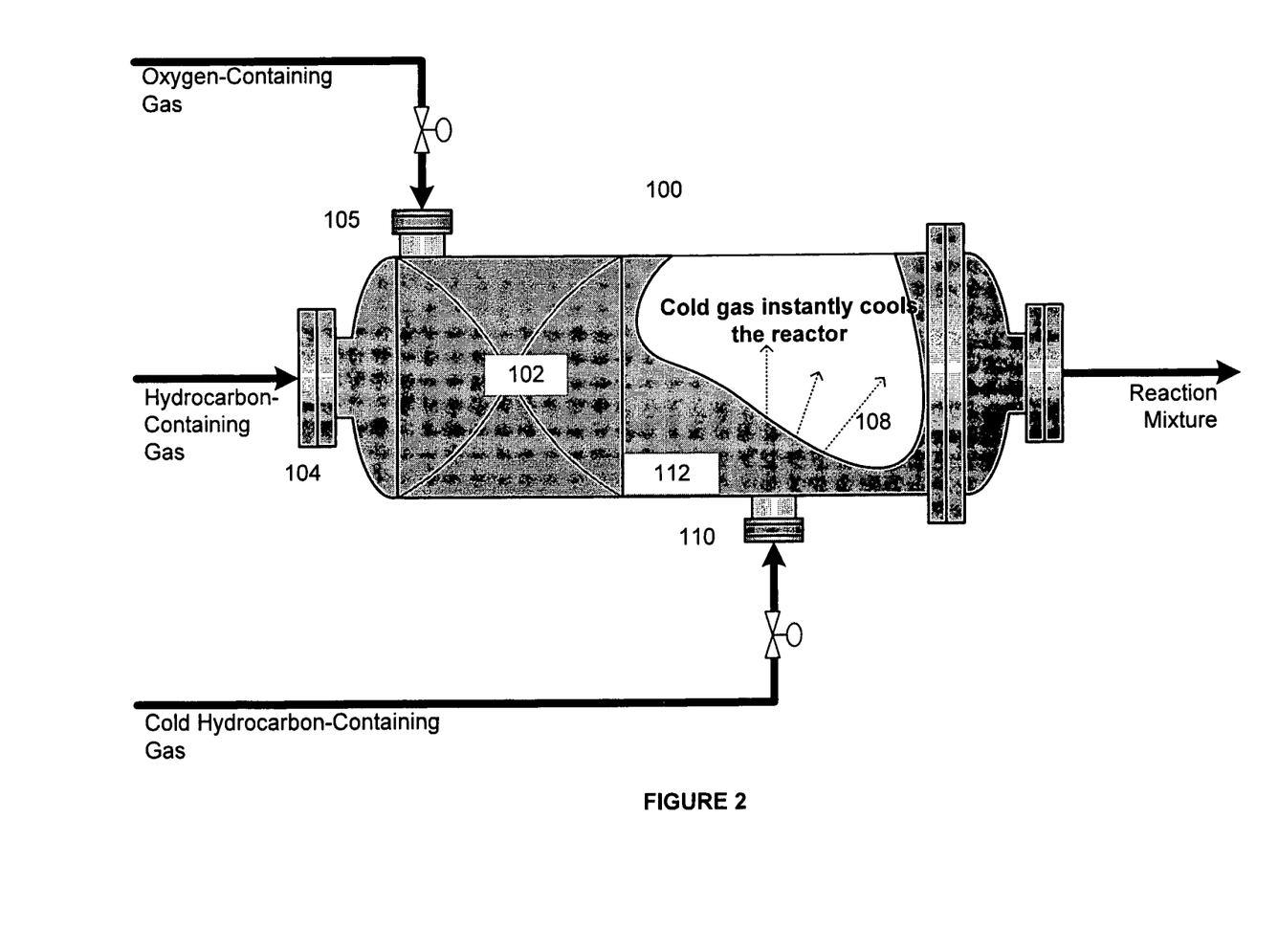
FIG. 2 illustrates a more detailed view of the reactor as shown in the system of FIG. 1.

As shown in the process flow diagram of FIG. 1, the system includes a reactor 100 which facilitates a gas phase direct partial oxidation of a methane-containing gas. FIG. 2 details the inputs and outputs of the reactor 100 as shown in the system of FIG. 1. The process begins with the reactor 100 where about, for example, 5% conversion of incoming alkanes is achieved having about 40% selectivity to methanol and about 25% selectivity to formaldehyde. The remaining balance of the reaction product is predominately carbon dioxide, following a gas-water shift reaction. The reactor 100 may have an initial reaction zone 102 that can be provided with a device 104 for introducing a heated methane-containing gas stream and a device 105 for introducing an oxygen-containing gas. As explained in more detail below, the oxygen-containing gas preferably has greater than 80% oxygen content to reduce the accumulation of inert gases due to the recycling process.

The reactor 100 may further be equipped with a regulation zone 108 provided with an optional device 110 for introducing a cold hydrocarbon-containing gas stream for reducing the temperature of reaction during operation of the apparatus. In addition, the reactor 100 may be provided with thermal pockets 112 for control and regulation of temperatures in corresponding zones, provided for example with thermocouples. Exiting the reactor 100 is a reaction product gas stream 1 which is at a temperature of about 525° C. and a pressure of about 8 MPa.

With reference to FIG. 1, stream 1 typically enters a "hot in" side of a first heat exchanger 114 that acts as a pre-cooler before the reaction product gas stream enters the absorption phase of the system. The heat exchanger 114 may be sized in order to maximize the heat integration taking place. Stream 2 exits a "hot out" side of the exchanger at a temperature of about 325° C. and is directed to a scrubber 116 for product and side-product recovery. In certain embodiments, stream 2 may be directed to a second heat exchanger, or pre-cooler (not shown), to further reduce the cooling load on the scrubber loop.

The scrubber 116 serves as the liaison between the reaction and recycling gas-phase raw material process, the liquid-phase separation, and the product rectification portion of the overall system. The scrubber 116 prevents the accumulation of $CO_2$ in the hydrocarbon recycle loop while concurrently facilitating the physical capture of formaldehyde. The scrubber 116 of the present disclosure further provides for the condensation of methanol and water that is produced in the reactor and present in the reactor product gas stream, reducing the number of separations within the hydrocarbon recycle loop to a single separation.

Figure 3:
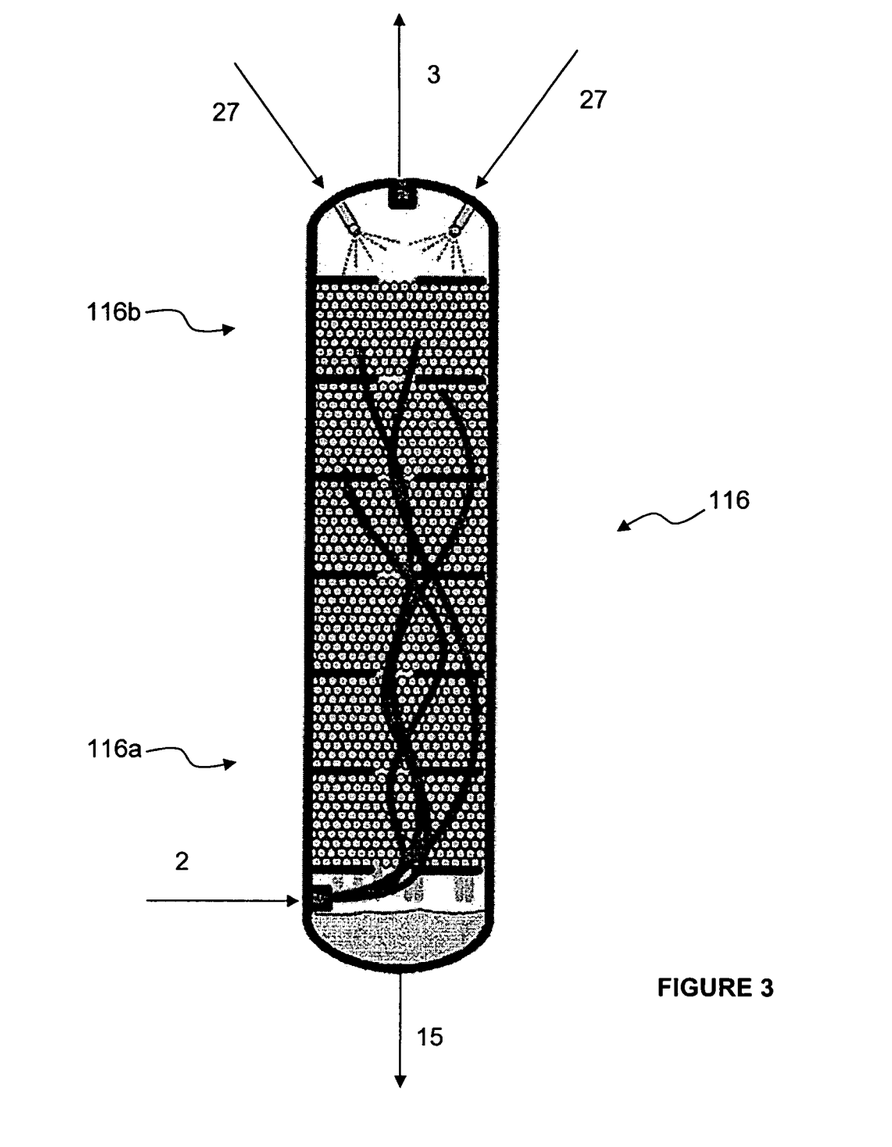
FIG. 3 illustrates a more detailed view of the scrubber as shown in the system of FIG. 1.

FIG. 3 details the inputs and outputs of the scrubber 116 as shown in the system of FIG. 1. The scrubber 116 may utilize a solvent/absorbent that comprises a mixture of reaction product components, namely methanol and water, to physically absorb formaldehyde and $CO_2$ from the hydrocarbon gas recycle loop. The efficiency of the scrubber 116 is enhanced by a combination of high operating pressure (4-8 MPa) and low temperatures, for example 25° C. or lower as needed to achieve the desired degree of absorption. As mentioned, the scrubber 116 additionally serves a duel role as a condenser. Both methanol and water will be substantially entrained into the recycling/regenerating absorbent stream. It is envisioned that this design reduces capital costs (due to simplification of the process), operational costs (due to more efficient cooling via direct contact), and the physical size of the process (due to less equipment).

In various embodiments, the lower portion 116a of the scrubber 116 operates at a higher temperature relative to the top portion 116b. It is envisioned that any water content will be removed prior to reaching areas of the column that are cold enough to allow the formation of ice. Since the scrubber 116 does not operate near the triple point of water, the incoming gaseous water will condense and not freeze. As is known, all liquids within the scrubber travel downward. In certain embodiments, it may be beneficial to provide a cooling jacket around the bottom portion of the scrubber.

The regeneration of the absorbent may be accomplished in a variety of ways. In one embodiment, a portion of the pregnant liquid stream 15 may be directed to a cooler 118 via stream 24 to serve as the regenerated, or fresh absorbent in stream 27. In various embodiments, a side-stream may be pulled off of this loop via stream 16 so as to prevent saturating the recycling stream with carbon dioxide and formaldehyde which will be loosely associated with the methanol-water mixture via physical absorbtion. In terms of a mass balance, the side-stream may include substantially all of the water, carbon dioxide, formaldehyde, and methanol entering the scrubber at steady state. Due in part to the known fact that some methanol is expected to escape the scrubber 116 via stream 3 and be recycled to the reactor 100, it may be beneficial to provide a methanol makeup stream, such as stream 22 that combines with the recycling pregnant absorbent stream 24 to form stream 23.

The clean, gaseous hydrocarbons of stream 3 can continue to a hydrocarbon recycle loop for further processing. In one embodiment, the next step may include a purge; for example, stream 18 that may be used to control any nitrogen accumulation within the recycle loop. Stream 4 may then continue to be combined with fresh, raw methane-containing gas, stream 5, to form a mixture via stream 6 that enters a recycle loop compressor 120 to recover any pressure losses from the processing units. In certain embodiments, an additional compressor 122 may be provided to compress the raw methane-containing gas prior to forming stream 6. Exiting the compressor is stream 7 that enters a heat exchanger 114 via a "cool in". The heated gas, which may reach a temperature of about 275° C., exits the as a "cool out" via stream 8 and may be directed to pre-heaters as discussed below.

The reactor 100 is preferably in communication with a compressor 124 and heater 126 for the supply of compressed and heated oxygen-containing gas at about 8 MPa and about 475° C. via streams 13 and 14, respectively. As mentioned, the raw methane-containing gas is mixed with recycled methane gas from the scrubber 116 and stream 9 may be heated using a pre-heater 128 to heat the gas to about 475° C. prior to entry in the reactor via stream 10. In the event the raw hydrocarbons have a high $CO_2$ content, a portion of the raw hydrocarbons in stream 7 can be mixed with the cooled reaction product gas stream, stream 2, at some point prior to the entry into the scrubber 116 for removal of contaminant gases prior to entering the reactor 100.

In operation, the raw methane-containing gas stream, having a methane content of up to about 98%, and the reduced methane product stream are supplied from their respective source to the pre-heater 128, where the gas is heated to temperature between about 430 to about 470° C. The heated methane-containing gas is then supplied into zone 102 of the reactor 100. Compressed air having a pressure of about 7-8 MPa and with a ratio of about 80% to 100% and, preferably, from about 90% to about 95% oxygen is supplied by the compressor 124 into zone 102 of the reactor 100. In order to limit the amount of $N_2$ within the system, for example to less than about 30%-40%, or to reduce the requisite size of the purge stream to achieve the same, the $O_2$ stream is preferably substantially pure, thus limiting the amount of $N_2$ entering the system.

In various embodiments, an optional second stream of cold methane-containing gas 11, or in other words a coolant at a lower temperature than the gases in the reactor, is supplied through the introducing device 108 into the regulation zone of the reactor 100. This stream is typically regulated by a regulating device 130 that can take the form of any suitable gas supply regulating device, regulating valve, or the like. In various other embodiments, this cold stream, or coolant can comprise a raw hydrocarbon stream, a recycled stream, or a portion or combination of the two. The regulator 130 may be configured to adjust a volume or pressure of a coolant based on system parameters including, but not limited to, pressure, temperature, or reaction product percentages downstream in the system.

The coolant is typically supplied from a coolant source, and if used, functions to reduce the temperature of the partially oxidized methane so as to reduce or limit the continued oxidation or decomposition of formaldehyde. This coolant can comprise any material that is easily separated from the reaction product stream. For example, as better described below, the coolant can include an unheated hydrocarbon or methane-containing gas stream. Additionally, the coolant can comprise any non-oxidizing material that can be easily separated from the reaction. In this regard, the coolant can be gaseous or an aerosol liquid including, for example, carbon dioxide, formaldehyde, methanol, ethanol, water, misted water, steam, and mixtures thereof. It is additionally envisioned that the coolant can be a mixture of recycled reaction products, water, steam, and/or hydrocarbon gases.

Depending on the intended mode of operation of the system, in particular the intended production of methanol or methanol and formaldehyde, the reaction mixture is subjected to the reaction in the reactor 100 without the introduction of the cold hydrocarbon-containing gas if it is desired to produce exclusively methanol. The introduction of the cold hydrocarbon containing gas is used when it is desired to produce methanol and formaldehyde. By introduction of the cold hydrocarbon-containing gas, the temperature of the reaction is reduced for example by 30-90° C. so as to preserve the content of formaldehyde into the separated mixture by inhibiting the decomposition of the formaldehyde to $CO_2$.

A formaldehyde rectification column 132 may be used to separate carbon dioxide and formaldehyde from methanol and water. In various embodiments, the formaldehyde rectification process may involve a flash drum (not shown), a column, or a combination depending on the desired product specifications. In certain embodiments, methane may be absorbed by the absorbent mixture; therefore, a flash drum 140 may be added to the regenerating absorbent loop, fed by stream 28, where the pressure of the stream 25 is dropped to accommodate the disassociation of any dissolved methane. This method will allow the absorbed methane gas to be returned to the hydrocarbon recycle loop. In other embodiments, any absorbed methane may be allowed to remain in solution where it will later be recovered with the exiting $CO_2$ stream and likely incinerated for heating value and/or elimination of any potential VOC's. A single column with a small reflux ratio may be sufficient to disassociate formaldehyde from the absorbent methanol-water mixture. As illustrated in FIG. 1, the pregnant methanol stream, stream 16, enters the rectification column 132 and is separated into a formaldehyde distillate, stream 17, and a bottoms stream, stream 18. It may be desirable to have a certain amount of methanol in the distillate stream since methanol is used as a stabilizer for the production of commercial grade formalin (6-15% alcohol stabilizer, 37% formaldehyde, and the balance being water), as discussed below. By allowing a portion of the heavy key into the distillate stream the separation is more easily achieved; furthermore, process losses typically experienced during absorbent regeneration may subsequently be nullified as methanol within the distillate is used in formalin makeup. Carbon dioxide may also escape at this point and travel with the formaldehyde stream to a formalin blender 136 via stream 17. In various other embodiments, a substantially pure stream of carbon dioxide may be removed for further processing. The remaining methanol-water mixture is directed to a methanol rectification section of the system via stream 18.

Methanol rectification may include one or two columns 134, depending on the desired specifications for the final methanol product. Methanol exits the rectification column via stream 19, of which a portion may be used for the methanol makeup stream of the scrubber loop, stream 22. The remaining methanol may be sent to storage. In embodiments where two columns are used, the methanol makeup, stream 22, would typically be taken from the distillate of the first column. As before, it is desirable for a portion of the heavy key to enter the distillate stream, as will be dictated by the commercial specification for formalin. For methanol rectification, 99% or higher purity is typical and 99.999% is achievable with multiple columns. The bottoms, stream 20, exit the column in liquid phase. Stream 20 may include some amount of ethanol (and perhaps methanol, if ultra pure methanol was produced) and will be used as the basis of the aqueous makeup of the commercial formalin, Stream 21. In this manner, some of the ethanol may be recovered before the remainder is discarded in the liquid waste stream.

The formalin blender 136 combines stream 17 with a side stream of the waste water, stream 21, to produce formalin (37% formaldehyde, 6% alcohol by weight). This takes place at reduced pressures such that carbon dioxide will not readily absorb into the water-alcohol mixture. Formaldehyde, on the other hand, is completely miscible with the mixture. Similar to the scrubber, gases are passed over falling liquids, wherein formaldehyde enters into an aqueousstate, thus becoming formalin. The product stream continues on to storage and the carbon dioxide stream can be sequestered, processed, or incinerated and then vented.

While the disclosure has been illustrated and described as embodied in the method of and apparatus for producing methanol, it is not intended to be limited to the details shown, since various modifications and structural changes may be made without departing in any way from the spirit of the present disclosure.

What is claimed is:

1. A method for recycling unreacted methane gas from a reaction product gas stream of a homogenous direct partial oxidation methane reactor, the method comprising:
    mixing a non-oxidizing coolant with a mixture of methane-containing gas and oxygen-containing gas to inhibit decomposition of formaldehyde while forming the reaction product gas stream, the non-oxidizing coolant including an unheated hydrocarbon or methane-containing gas stream;
    feeding the reaction product gas stream into a scrubber;
    passing a pre-cooled absorbent through the scrubber;
    cooling the reaction product gas stream via direct contact with the pre-cooled absorbent through the scrubber;
    removing unreacted methane gas from the reaction product gas stream using the pre-cooled absorbent;
    recycling the unreacted methane gas for use in the homogenous direct partial oxidation methane reactor; and
    recycling the pre-cooled absorbent for reuse in the scrubber, wherein the pre-cooled absorbent comprises process components of the reaction product gas stream, the scrubber having a lower portion and an upper portion, the temperature of the lower portion being higher than the temperature of the upper portion, the scrubber being further configured such that all liquids flow downward.

2. A method according to claim 1, wherein the scrubber operates at a pressure of at least about 4MPa and at a temperature of less than about 0° C.

3. A method according to claim 1, wherein the reaction product gas stream comprises a mixture of methanol, formaldehyde, and carbon dioxide, and the pre-cooled absorbent comprises a mixture of methanol and water.

4. A method according to claim 3, further comprising maintaining a steady state balance of methanol between the scrubber and the homogenous direct partial oxidation methane reactor by adding recycled methanol to the scrubber.

5. A method according to claim 3, further comprising condensing methanol and water from the reaction product gas stream and separating a fraction of methanol and water as an absorbant.

6. A method according to claim 3, further comprising substantially removing all of the methanol and formaldehyde entering the scrubber at steady state via a side removal stream.

7. A method according to claim 3, further comprising cooling the spent absorbent prior to its reintroduction in the scrubber.

8. A method for producing methanol using a homogenous direct partial oxidation reactor, the method comprising:
    feeding the reactor with a methane-containing gas and an oxygen-containing gas;
    carrying out partial oxidation reaction of methane to form a product gas comprising a mixture of methanol and formaldehyde;
    mixing a non-oxidizing coolant with the methane-containing gas and oxygen-containing gas to inhibit decomposition of formaldehyde, the non-oxidizing coolant including a hydrocarbon or methane-containing gas stream;
    directing a pre-cooled absorbent to a scrubber;
    directing the product gas to said scrubber;
    cooling the product gases via direct contact with pre-cooled absorbent within the scrubber;
    scrubbing the product gas with said pre-cooled absorbent comprising process components of the product gas in a scrubber, the scrubber having a lower portion and an upper portion, the temperature of the lower portion being higher than the temperature of the upper portion, the scrubber being further configured such that all liquids flow downward;
    removing methanol, water, carbon dioxide, and formaldehyde from the product gas to form a spent solvent;
    recycling unreacted methane-containing gas from the product gas into the homogenous direct partial oxidation methane reactor; and
    recycling spent solvent for reintroduction into the scrubber as the pre-cooled absorbent.

9. A method according to claim 8, wherein the pre-cooled absorbent comprises methanol and water.

10. A method according to claim 9, wherein recycling the spent solvent comprises substantially removing all of the methanol, water, carbon dioxide, and formaldehyde entering the scrubber at steady state via a side removal stream.

11. A method according to claim 9, wherein recycling the spent solvent comprises cooling the solvent prior to its reintroduction in the scrubber as an absorbent.

12. A method according to claim 9, further comprising cooling the product gas prior to directing the product gas to the scrubber.

13. A method according to claim 9, wherein the product gas is scrubbed at a pressure of at least about 4 MPa and at a temperature of less than about 0° C.

* * * * *